United States Patent [19]

Kugel

[11] Patent Number: 5,634,931
[45] Date of Patent: Jun. 3, 1997

[54] HERNIA MESH PATCHES AND METHODS OF THEIR USE

[75] Inventor: Robert D. Kugel, Chehalis, Wash.

[73] Assignee: Surgical Sense, Inc., Arlington, Tex.

[21] Appl. No.: 315,249

[22] Filed: Sep. 29, 1994

[51] Int. Cl.$^6$ .................................................. A61B 17/00
[52] U.S. Cl. .......................... 606/151; 606/1; 606/213
[58] Field of Search .................................. 606/151, 200, 606/213, 1, 110, 113, 114, 127; 623/11; 128/899; 602/58

[56] References Cited

U.S. PATENT DOCUMENTS

| 2,671,444 | 3/1954 | Pease, Jr. |
|---|---|---|
| 3,054,406 | 9/1962 | Usher. |
| 4,347,847 | 9/1982 | Usher. |
| 4,452,245 | 6/1984 | Usher. |
| 4,561,434 | 12/1985 | Taylor ........................ 602/58 |
| 4,854,316 | 8/1989 | Davis ........................ 128/899 |
| 5,059,205 | 10/1991 | El-Nounou et al. ........ 606/200 |
| 5,116,357 | 5/1992 | Eberback ................... 606/213 |
| 5,122,155 | 6/1992 | Eberbach ................... 606/213 |
| 5,147,374 | 9/1992 | Fernandez .................. 606/151 |
| 5,147,384 | 9/1992 | La Rocca ................... 606/234 |
| 5,254,133 | 10/1993 | Seid ......................... 606/215 |
| 5,258,000 | 11/1993 | Gianturco .................. 606/151 |
| 5,290,217 | 3/1994 | Campos ..................... 606/151 |
| 5,318,559 | 6/1994 | Mulhanser .................. 606/1 |
| 5,370,650 | 12/1994 | Tovey et al. ............... 606/151 |

Primary Examiner—Michael Powell Buiz
Assistant Examiner—Jeffrey A. Schmidt
Attorney, Agent, or Firm—James E. Bradley

[57] ABSTRACT

Surgically implantable hernia mesh patches are available in several embodiments, wherein each embodiment has double like size layers of inert synthetic mesh material, compressibly positioning an internally positioned loop of a resilient monofilament fiber, when these double layers of mesh are sewn together around their edges, while leaving one centimeter free of both top and bottom layers of mesh. During operating time of a surgical repair of an inguinal hernia, one of these hernia mesh patches is compactively arranged and then inserted through a relatively small incision, for subsequent planar expansion and directed placement to where the hernia is, usually under minimal anesthesia, without the need for entering a patient's abdominal cavity, and without the need to use instrumentation, such as laparoscopic equipment. One of the double layers has a transverse slit for the insertion of a surgeon's finger between these layers of mesh, which facilitates a surgeon's maneuvering and positioning of these double layers of mesh, being always expanded by the loop of resilient monofilament fiber, within a patient's preperitoneal pocket volume to serve as this surgical patch without sutures. The other embodiments have very worthwhile additive features.

20 Claims, 2 Drawing Sheets

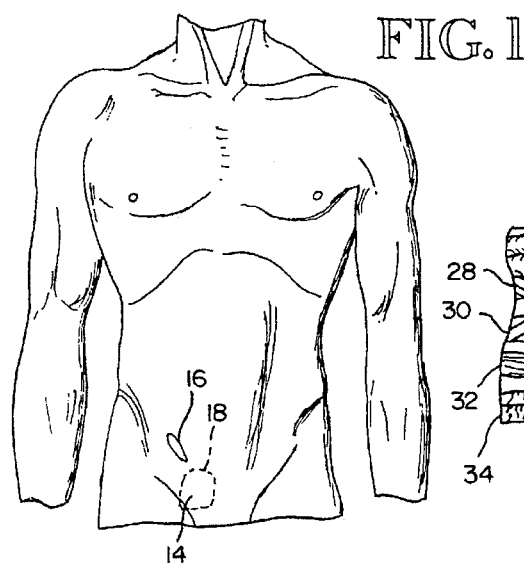
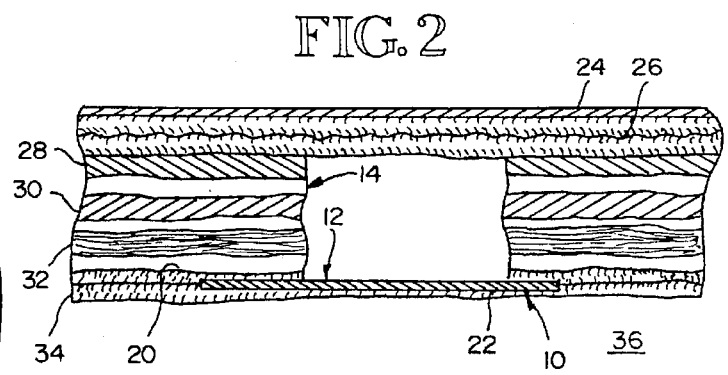
FIG. 1
FIG. 2
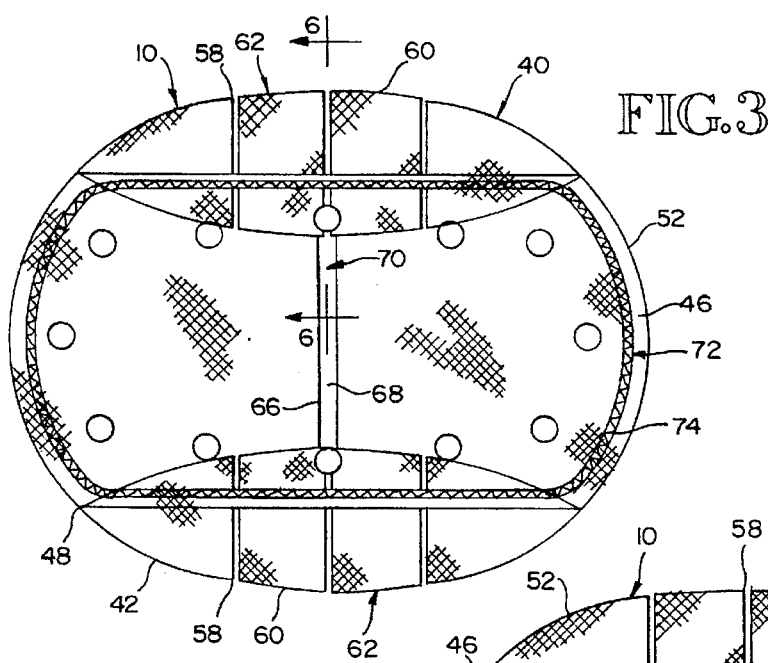
FIG. 3
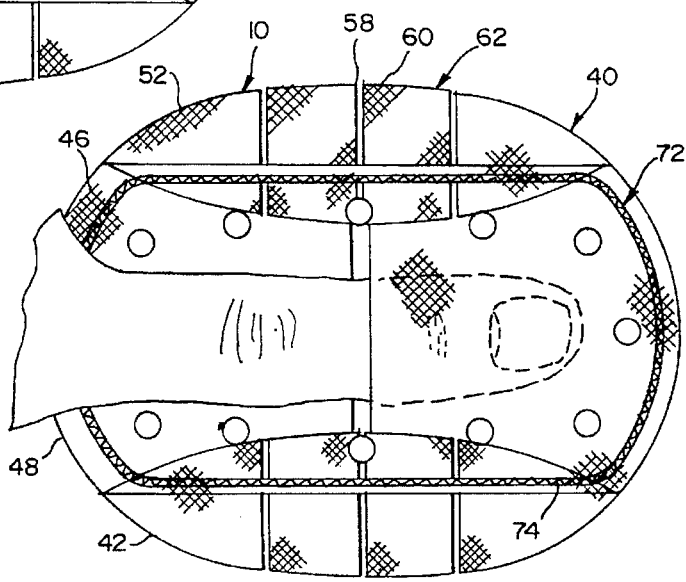
FIG. 4

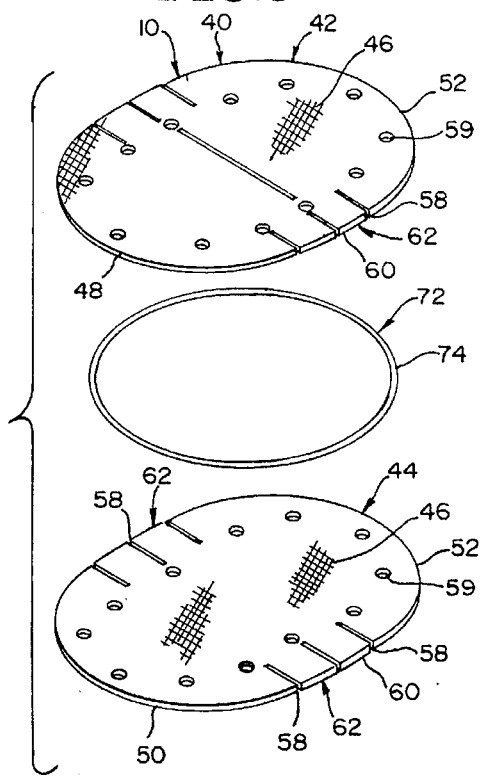
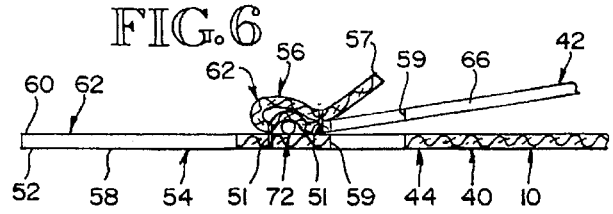
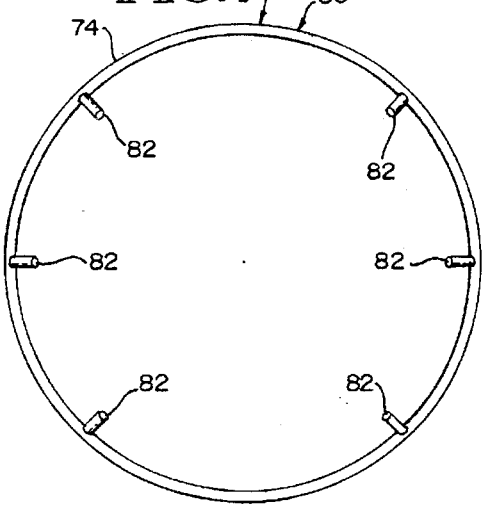
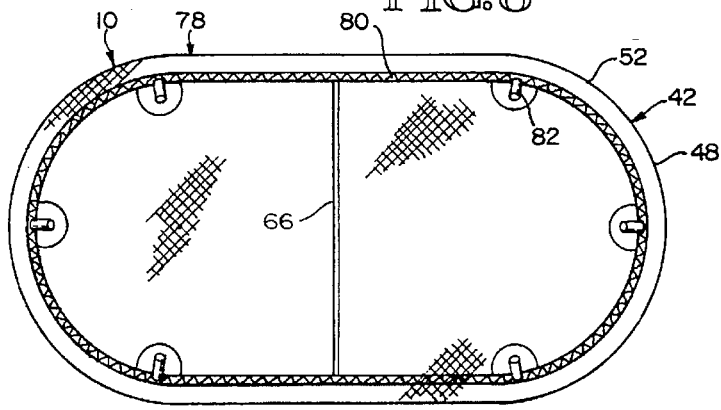
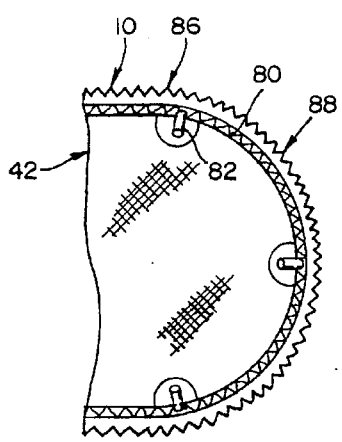

HERNIA MESH PATCHES AND METHODS OF THEIR USE

BACKGROUND

Surgically implantable mesh patches for the repair of inguinal and other abdominal wall hernias, which are intended for permanent placement within a patient's body space, have been provided and used previously as set forth, for examples, in the following U.S. patents:

In 1954, Benjamin F. Pease, Jr., in his U.S. Pat. No. 2,671,444 illustrated and described his nonmetallic mesh surgical insert for hernia repair, comprising a sheet of relatively fine uniform open mesh work of a durable, permanently pliable, non-toxic radiation permeable resinous material, which was compatible with body tissues and fluids, and inert chemically with respect thereto. All the joints of the mesh work were preferably unitary, in consequence of which the surgeon could trim the she, of open mesh work to any desired size and shape, without any danger of it unraveling. The cut edge provided an adequate strong portion for suturing the mesh work to the patient's body tissues at any convenient location. The mesh work itself promoted the ready growth therethrough of the patient's own repair tissue. The mesh work insert was adapted to remain permanently in the patient's body, facilitating the body's own efforts to repair the hernia, and minimizing the chance of reoccurrence, without the danger of future difficulties because of irritation, corrosion, or the like.

In 1962, Francis C. Usher in his U.S. Pat. No. 3,054,406, illustrated and described his improved surgical mesh which was intended to be held in place by sutures. This surgical mesh was made of a polyethylene thread, free of water leachable irritant impurities and having a tensile strength of at least 50,000 p.s.i., and a weight from 100 to 500 denier. The threads of the improved surgical mesh were spaced at intervals in the range of 5 to 50 mils. These threads were unattached to each other at their points of crossing. This improved surgical mesh was physiologically inert even in the presence of any possible infection.

In 1982, Francis C. Usher in his U.S. Pat. No. 4,347,847, continued describing and illustrating his improvements in providing surgical mesh and the method of the use thereof in hernia repair. In his method of repairing hernias and other defects of the abdominal and chest wall, he placed a tubular surgical mesh over the defect in its flattened form to provide continuous border edges. The tubular surgical mesh was of a size sufficient to bridge the defect, and to position the continuous border edges thereof on tissue adjacent the opposite sides of the defect, free of selvage edges. He then sutured through the mesh adjacent the continuous border edges to the tissue. The surgical mesh was comprised of monofilament threads which were free of water leachable irritant impurities and were physiologically inert, even in the presence of infection. The monofilament threads had a tensile strength sufficient, when doubled, to withstand wound tension. The threads of the mesh had a diameter in the range of 5 to 15 mils. The mesh was formed having 10 to 20 stitches per inch, and during the formation a continuous tubular shape was created. The threads were unattached to each other at their points of crossing. The threads were made of a polypropylene monofilament.

In 1992, Mark A. Eberbach in his U.S. Pat. No. 5,116,357, illustrated and described his hernia plug and introducer apparatus. Mr. F. Eberbach provided, via a laparoscopic system, a plug and patch assembly comprising a cylindrical plug of flexible material, positionable in an opening in the abdominal wall to be repaired, with the plug being in contact with the opening. The plug had a distal end and a proximal end. Then there was a patch of an inextensible and flexible mesh material to be positioned over weakened portions of the abdominal wall adjacent to the opening. A central extended portion of the patch was coupled to the proximal end of the cylindrical plug, with the periphery of the patch being remote from the plug, and constituting a flange. Then a resilient small cross-sectional diameter adjustable loop of ribbon material, constructed of surgically antiseptic material, was used to keep the patch extended in the intended location thereof, both over and beyond the weakened portions of the abdominal wall. A surgeon using conventional laparoscopic techniques finally positioned the patch, after the initial placement of this loop of ribbon material.

Also in 1992, Mark a Eberbach in his U.S. Pat. No. 5,122,155, illustrated and described another of his hernia repair apparatus and method of use. His laparoscopic repair of abdominal hernias by a surgeon, through patching of a weakened portion of the abdominal part to be repaired, comprised the steps of:

"providing a patch formed of flexible, inextensible material and positionable in a plane adjacent to the weakened portions of the abdominal part to be repaired, the patch having an elongated passageway located in the plane of the patch adjacent to the majority of the periphery of the patch, the passageway having an opening at one end thereof;

providing an elongated interior ribbon having a distal end positioned through the opening of the passageway and slid able within the passageway, the ribbon being sufficiently rigid whereby it may be remotely pushed into the passageway;

providing an elongated intermediate cylindrical plunger having an interior slid ably receiving the ribbon, the plunger having a distal end coupled to the patch and a proximal end to be manipulated by the surgeon;

providing an elongated exterior cylindrical sheath having an interior slid ably receiving the plunger, the ribbon and the patch, the sheath having a distal end adjacent to the patch and a proximal end to be manipulated by the surgeon, the sheath being of a length to extend from exterior of a patient through a laparoscopic port into a surgical cavity which includes the part to be repaired;

positioning the patch and the distal ends of the ribbon, plunger and sheath into a patient adjacent to the area to be repaired;

advancing the patch and plunger from the sheath;

advancing the ribbon into the passageway of the patch to expand the patch;

coupling the patch to the area to be repaired;

withdrawing the ribbon from the patch;

separating the patch from the plunger; and withdrawing the ribbon, plunger and sheath from the patient."

Also in 1992, Alfredo Fernandez illustrated and described his prosthetic mesh patch for laparoscopic hernia repair. His mesh patch, which was inserted through the opening in the patient to be repaired, was a rolled up sheet of surgical plastic mesh maintained in a rolled up form by attaching at least two bands around it. Then he made multiple longitudinal cuts in the first end of this rolled up mesh to form multiple flared out flaps. The flaps were then stitched to a planar sheet of plastic surgical mesh. The overall patch was then inserted into the patient's opening, by using a second end of the rolled up sheet of surgical plastic. In this way, the rolled portion of the patch entered the patient's opening, and the flaps and the planar sheet of plastic surgical mesh were displayed out over an entrance to the patient's opening. Thereafter the planar sheet of plastic surgical mesh was stapled to adjacent tissue of the patient to retain the patch in position; and In 1993, Arnold S. Seid in his U.S. Pat. No. 5,254,133 illustrated and described his surgical implantation device and related method of use to seal an enlarged, generally circular opening in the wall of one of the patient's body cavities. He provided a surgical implantation device having a generally planar first portion and second portion which were interconnected by a connecting segment. He then inserted and located one end of a surgical tube through the patient's wall opening and adjacent a first side of the wall. Then be forced the first portion of the surgical implantation device out of the surgical tube adjacent the first side of the wall, and allowed this first portion to automatically assume a planar shape. Thereafter he forced the connecting segment of the surgical implantation device out of the surgical tube to be within the wall opening. Subsequently, he forced the second planar portion of the surgical implantation device out of the surgical tube adjacent a second side of the wall, and allowed this second portion to automatically assume a planar shape. Then he passed a suture through the first portion, the connecting segment, and the second portion of the surgical implantation device, and tied off the suture to attach these three portions together. Finally, he withdrew the surgical tube from the patient. Resilient members were respectively attached to either the first of the second portions, which were initially flexible enough to be folded into the surgical tube. Thereafter, when they were cleared from the surgical tube, they unfolded into a planar orientation with their respective first or second portions.

These inventors in illustrating and describing their patches and their ways of using their patches, led the way of creating tension free surgical repairs of hernias using synthetic mesh materials to bridge and to patch hernia defects. These repairs resulted in both a decrease in the recurrence rate as well as a decrease in the amount of a patient's post operative discomfort. Patients undergoing these more advanced procedures were able and are able to resume their normal activities sooner. As realized, some of these earlier inventions are somewhat complicated or are complicated. Several use some type of a plug or a locating member to fit within the hernia defect itself. Also many of these earlier inventions were designed specifically for use in laparoscopic repair of hernias. Moreover, many of the prior inventions regarded their suturing to the patient's body tissue. Although these medical advances are acknowledged for their usefulness and success, there remained a need or needs for more improvements in the surgical repair of hernias.

SUMMARY

A hernia mesh patch for use in the sutureless surgical repair of a patient's inguinal, or other abdominal wall hernias, is available for relatively low cost and simplified surgical permanent placement within a patient's body space. This hernia mesh patch has top and bottom layers of an inert, synthetic mesh, preferably polypropylene mesh, sewn to each other at approximately one centimeter from their outer edges. The top layer has a transverse cut or slip opening into the interior pocket or pouch volume of this patch. Then to serve a spring function, an implantable inert monofilament fiber, arranged in an oval, ovoid, loop, or ring configuration, having a circumference slightly greater than the circumference of the interior pocket volume of this patch, is inserted into this pocket to keep the hernia mesh patch expanded under tension in a planar configuration.

Then without the need for general anesthesia, nor expensive laparoscopic instrumentation, a surgeon, when repairing an inguinal hernia, makes a small incision in the patient, approximately three centimeters long, arranged obliquely, approximately two to three centimeters above the internal ring location of the inguinal hernia. Through this small incision, using the muscle splitting technique, the surgeon performs a dissection deep into the patient's preperitoneal space, creating a pocket in this space into which this hernia mesh patch is to be inserted.

Thereafter, the surgeon, using his or her fingers, readily folds and compacts this hernia mesh patch and directs it through the incision and into the patient's preperitoneal space, where it unfolds and expands into its planar configuration, creating a trampoline effect. Then the surgeon, using just one of his or her fingers, placed partially through a slit in the top layer of mesh and into the pocket or pouch between the top and bottom layers of this hernia mesh patch, conveniently and accurately moves the hernia mesh patch to cover the defect in the patient's thick reinforcing lining of his or her abdominal cavity. Thereafter the surgeon withdraws his or her finger and then secures the incision with stitches.

The patient's post-operative discomfort is decreased, and risk of any recurrence is likewise decreased. The patient's body, soon after surgery, reacts to the mesh of the hernia mesh patch, and in a short time, the mesh becomes stuck, thereby keeping the hernia mesh patch in place. Thereafter the patient's scar tissue grows into the mesh over a period of time, between thirty and sixty days, to permanently fix the hernia mesh patch in its intended position over the repaired area, where the hernia was located.

The hernia mesh patches are made in several sizes. Four standard sizes accommodate ninety percent of the inguinal and abdominal wall hernias. With respect to repairing inguinal hernias, the most appropriate size is eight by ten centimeters.

The diameter of the monofilament fiber, which is preferably made from nylon, polypropylene, or polyester, and arranged to subsequently serve as a spring, is adjusted in size in respect to the selected size of the hernia mesh patch to be used. A large diameter fiber is used in the spring of a larger diameter mesh patch to make the hernia mesh patch stiffer. While allowing for the sufficient stiffness to insure the hernia mesh patch will open to its predetermined overall dimensions, there must be adequate flexibility to allow this hernia mesh patch to conform to the patient's uneven body contours and surfaces, and initially to allow for the folding and compacting of the hernia mesh patch for its insertion through the small entrance incision. In respect to all sizes of these hernia mesh patches, the presence of the monofilament fiber spring also allows for the use of a smaller diameter mesh fiber, which might otherwise be necessary to provide the necessary stiffness in a patch not having such a fiber spring.

In respect to large hernia mesh patches, the spring may include the winding of two or more monofilament fibers. Also large hernia mesh patches are initially kept from sliding by using a limited number of anchoring stitches. They are placed without creating tension, without significantly increasing a patient's post-operative discomfort, and without contributing to the strength of the overall surgical repair of the patient's hernia.

Regarding the one centimeter, initially free outer edges of the respective top and bottom layers of the mesh material, they are slit in radial cuts to create scalloped or fringed edges. The bottom layer flat scalloped edges serve to fill uneven voids in the patient's tissue surface, which helps to minimize any risk of the patient's tissue slipping over this patch and allowing the hernia to recur. The top scalloped edges are folded back and sewn along the monofilament fiber spring, leaving some portions of their folded over scalloped edges free to subsequently resist the migration of this hernia mesh patch, after it has been inserted into the limited sized preperitoneal pocket or pouch developed by the surgeon under the patient's hernia defect. The hernia mesh patch held in its intended shape by the fiber spring completely fills enough of this pocket to completely extend over and beyond the patient's hernia defect. After its initial insertion, and thereafter, the patient's hernia mesh patch is held in position by the hydrostatic pressures created between the two tissue layers of fascia above the patch and the peritoneum below the patch.

In respective designs of these hernia mesh patches, small holes are cut through both layers of the mesh inside the fiber ring, to increase friction and to minimize the sliding or migration of the hernia mesh patch, after it is positioned. Also in some designs, spaced spikes are attached to the fiber spring, or are integrally formed with the fiber spring to serve as anchors, by entering the patient's tissue. Also in some designs of these hernia mesh patches to be used in a location where the patient's peritoneum has been destroyed, one layer of this patient's hernia patch is made of a material, such as "Gortex" material, which is less prone to adhere to a bowel or other intra-abdominal organ.

In respect to all the hernia mesh patches, they have their simplicity of design and method of insertion. They adequately underlay a hernia defect by a minimum of two centimeters around the circumference of the hernia defect, with sufficient rigidity and with sufficient friction to eliminate or minimize sliding or migration. When these hernia mesh patches are used, the repair of inguinal and other abdominal wall hernias are repaired through a smaller wound or incision, with less tension, less post-operative discomfort, shorter operating time, and at a potential lower cost to the patient.

DRAWINGS

FIG. 1 is a schematic partial front view of a patient's body indicating, in respect to the surgical repair of an inguinal hernia, where a three centimeter incision is made obliquely approximately two to three centimeters above the location described as the internal ring of the hernia, in reference to the location of an inguinal hernia;

FIG. 2 is a schematic partial diagrammatic cross-sectional view of a patient's abdominal wall layers showing an inguinal or other abdominal wall hernia, and where the surgically implantable hernia repair mesh patch has been correctly positioned in the preperitoneal created space;

FIG. 3 is a top view of a preferred embodiment of the surgically implantable hernia repair mesh patch, having anchoring or friction holes cut through both layers of the mesh, which after the surgical insertion of the surgically implantable hernia repair mesh patch, serve to minimize any risk of the mesh migrating or moving once positioned by a surgeon;

FIG. 4 is similar to FIG. 3, showing how a surgeon's finger is inserted through a slit, which is made by cutting through only the top layer of the two layers of mesh used in this surgical hernia patch, whereby a surgeon's finger, so inserted between these layers of mesh, then directs the movement of this surgical hernia patch through the incision and on to the location of the inguinal hernia;

FIG. 5 is an exploded view of the surgically implantable hernia repair mesh patch shown in FIGS. 2, 3 and 4, to show the two layers of the mesh, preferably cut from polypropylene mesh material, and also to show a resilient monofilament ring, which when located between the layers of mesh, becomes a resilient spring ring keeping the surgical hernia patch fully expanded;

FIG. 6 is a transverse cross sectional view of the center of the preferred surgically implantable hernia repair mesh patch, illustrated in FIGS. 2, 3, 4 and 5, with the top and bottom layers shown slightly separated for illustrative purpose, and showing how some of the bottom mesh materials extending free of the peripheral stitching are split, forming tab portions of mesh, and showing how some of the top mesh materials are first folded back and then sewn in place by the fold, while allowing the remaining split portions to remain free before use, and later both these top and bottom free split tab portions, during and after surgery, help in minimizing or eliminating any risk of the mesh migrating or moving once positioned by a surgeon;

FIG. 7 is a top view of another resilient monofilament ring, which becomes the located spring ring, showing how space anchoring monofilament spikes are secured to this ring or are made integral with this ring or are made integral with this ring;

FIG. 8 is a top view of another embodiment of the surgically implantable hernia repair mesh patch, which has the resilient monofilament ring, illustrated in FIG. 7, placed between the layers of mesh thereof, and the spaced anchoring monofilament spikes are extending diagonally upwardly, and they are located, where there are respective anchoring or friction holes, made through both layers of the mesh, and the top layer has the slit to accommodate a surgeon's finger; and FIG. 9 is a partial top view of another embodiment illustrating a circular surgically implantable hernia repair mesh patch having the resilient monofilament spring ring with spikes, spaced anchoring holes, and irregular cut edges of both the top and bottom layers of mesh, where they extend beyond the stitching, and also a slit for receiving a finger of a surgeon.

DESCRIPTION OF THE PREFERRED EMBODIMENTS

The Surgical Method of Preparing to Use the Hernia Mesh Patch to Repair an Inguinal Hernia The hernia mesh patches 10, illustrated in the drawings, are surgically permanently implantable within a patient's body space 12 to adequately cover, correct, and repair any inguinal or other abdominal wall hernias 14. The surgeon has the objective of making a sutureless repair, by first cutting an approximately three centimeter incision 16, obliquely positioned approximately two to three centimeters above the location described as the internal ring 18, where an inguinal hernia 14 has occurred, as shown in FIG. 1. Then the surgeon working through this incision 16, and using a muscle splitting technique, dissects deeply into the patient's preperitoneal space 20, entering slightly superior and posterior to the patient's hernia defect 14. The surgeon then creates a pocket 22 in the patient's preperitoneal space 20, into which the hernia mesh patch 10 is inserted, as shown in FIG. 2.

The surgeon in dissecting deeply into the patient's peritoneal space 20, as indicated in FIG. 2, will have used a sharp instrument to make the incision or wound 16 through the patient's skin 24, the subcutaneous fatty tissues 26, and the external oblique fascia 28, which has been cut parallel with its fibers a short distance. Then the surgeon has incised the transversalis fascia 32, creating an entrance into the preperitoneal space 20, above the peritoneum 34 at a location above the hernia 14. In so doing, the surgeon has identified and freed up the hernia sac and has created the pocket 22 in the preperitoneal space 20. This space 20 underlies the area referred to as Hesselbach's triangle, in reference to both indirect and direct hernias. The surgeon's placement of this hernia mesh patch 10, using this method, protects the entire inguinal floor, and therefore not only will it repair or correct a single small hernia, but will also protect against future hernias through other potentially weakened areas. In a similar way, a hernia mesh patch 10, sandwiched between a hernia 14, i.e. defect 14, and the inner lining 34, i.e. the peritoneum 34, of the abdominal cavity 36, is used to underlay a femoral canal area, not shown, through which femoral hernias occasionally occur. Wherever used, the hernia mesh patch 10, in its respective embodiments, serves as the basis for tension free surgical repair of a hernia, as it is used to patch and to bridge the hernia 14, i.e. the defect 14. The hernia mesh patch 10 is made, so after completing this preparation, the surgeon using his or her fingers, can fold and compact the hernia mesh patch 10 and insert it down through the incision 16 into preperitoneal space 20. Thereafter, using his or her finger, the surgeon expands, moves, and directs, the hernia mesh patch 10 into position in the pocket 20 within the preperitoneal space 20 to bridge the hernia 14, or defect 14.

The Hernia Mesh Patches, Compactly Folded and Inserted Through the Patient's Incision, and Then Expanded, Moved, and Directed, by a Surgeon Using His or Her finger, Into a Position to Patch and to Bridge the Hernia An embodiment 40 of these hernia mesh patches 10, is illustrated in FIGS. 2 through 6, which is particularly designed for the repair of an inguinal hernia 10. This embodiment 40 is coraposed of two similarly sized and shaped pieces 42, 44, of an inert synthetic mesh material 46, which preferably is a polypropylene material. This mesh material 46 is formed from monofilament material which is resistant to infection, and which has been used safely in many hernia operations, in previous ways and in previous embodiments. Preferably, the two similarly sized and shaped pieces of mesh material 42, 44 are made in respective circle, loop, ovoid, or oval shapes. One 42 of these pieces 42, 44, is referred to as the first or top layer 42 of the synthetic mesh material 46 and the other one 44 of these pieces 42, 44, is referred to as the second or bottom layer 44 of the synthetic mesh material 46. These two layers 42, 44, are sewn to each other approximately one centimeter in from their outer edges 48, 50 using a thread 51 of inert synthetic material. The outer one centimeter of mesh material 52 of the bottom mesh material piece or layer 44 is left free to serve as an apron 54 to fill uneven voids in the patient's tissue. The outer one centimeter of mesh material 52 of the top mesh material piece or layer 42 is folded back and sewn adjacent the fold 56, while leaving free the remaining portions of this outer one centimeter of mesh material 52 of this top mesh layer 42. Thereafter, this free portion 57, when the hernia mesh patch 10 has been placed in the preperitoneal space, serves to frictionally keep this patch 10 in its hernia 14 repair position. Also inside of the fold 56, like size holes 59, aligned one above the other, are cut respectively in the top and bottom mesh layers 42, 44. The presence of these holes 59 helps initially to frictionally keep the hernia mesh patch 10 in place. Thereafter the patient's scar tissues grow in and around these holes 59 to continue to keep the hernia mesh patch in position. The outer one centimeter of mesh materials 52 are both cut or slit 58, radially or diagonally creating scalloped or fringed edges 60 on respective flap, or tab portions 62, of both the outer one centimeter of mesh materials 52, of the top and bottom mesh layers 42, 44.

Also the top mesh material, or top layer piece 42, is cut or slit 66 transversely at the center 68 thereof, creating a finger access 66 into the interior space 70, or pouch 70, between the top and bottom layers 42, 44 of the synthetic mesh material 46. Through this slit 66, a ring like arrangement 72 of a continuous, inert, implantable, monofilament fiber 74, when squeezed temporarily to narrow it and to elongate it, is inserted into the interior space 70 or pouch 70. Then it is released, and allowed to expand, serving a spring function and therefore it is called a spring 72, while it is compressibly held in this interior space 70 or pouch 70 of the hernia mesh patch 10, thereby keeping this patch 10 fully extended in a planar arrangement, as shown in FIGS. 2, 3, and 4. This spring 72 is made of a synthetic material, such as nylon, polypropylene, or polyester. In each embodiment, this monofilament loop, ring or spring 72, has a circumference which is slightly larger than the circumference of the interior space 70, or pocket 70, or pouch 70, which is formed between the top and bottom layers 42, 44 of the synthetic mesh material 46.

Another embodiment, i.e. a second embodiment 78, is illustrated in FIGS. 7 and 8, wherein the ring or spring 80 has spaced monofilament spikes 82 secured to the ring 80, or made integrally with it. They are directed on an angle to extend above this embodiment 78 of a hernia mesh patch 10, to enter the patient's body tissue. In this way the continuing accurate location of this hernia mesh patch 10 is insured. The outer one centimeter of mesh material 52, as shown in FIG. 8, is not cut nor slit.

Another embodiment, i.e. a third embodiment 86, is illustrated in FIG. 9, wherein a portion of it is shown, indicating its similarity to the second embodiment 78, illustrated in FIGS. 7 and 8. However, the outer one centimeter of mesh materials 52 are cut to create scalloped or fringed circumferential edges 88, above and below, which also serve to frictionally hold the hernia mesh patch 10 in place, along with the spikes 82 on the loop, ring or spring 80.

These hernia mesh patches 10 in their various embodiments are made in several sizes. Generally four standard sizes accommodate ninety percent of the inguinal and abdominal wall hernias. Inguinal hernias are generally repaired by using a hernia mesh patch 10, which is eight centimeters wide and ten centimeters long.

The Surgical Method is Continued Using a Selected Embodiment of the Hernia Mesh Patch At the conclusion of the surgeon's use of both sharp and blunt instruments to create the pocket 22 in the preperitoneal space 20, he or she selects the type and size embodiment of the hernia mesh patch 10 best suited to be used in the repair of the patient's defect or hernia 14. The selected embodiment 40, 78 86 or another one, not shown, of the hernia mesh patch 10, is folded and further compacted, as may be necessary, by the surgeon using his or her fingers, so the selected patch 10 may be conveniently inserted through the wound or incision 16 and down into the preperitoneal space 20. In this space 20, the hernia mesh patch 10 is freed and allowed to expand under the force of the loop, ring, or spring 74. Thereafter the surgeon using his or her finger, continues any further expansion of this patch 10, which might be necessary. Then his or her finger is inserted through the cut or slit 66 in the center 68 of the top mesh layer 42, and the hernia mesh patch 10 through the preperitoneal space to the pocket 22. After the withdrawal of his or her finger, the surgeon completes the repair surgery by closing the wound or incision with stitches, in respect to this repair of an inguinal hernia, using the remote incision 16, as illustrated in FIG. 1.

In the repair of other hernias, and especially those that are large, a direct incision is made, and after the placement of a large hernia mesh patch 10, the surgeon may use limited sutures to keep the larger hernia mesh patch 10 in place. Generally, most of the embodiments of this hernia mesh patch 10 are positioned, and so remain, without the use of limited sutures.

In respect to the utilization of all of the embodiments of these hernia mesh patches 10, they have their simplicity of manufacturing design and of their surgical method of insertion. All these patches 10 adequately underlay a hernia 14 or defect 14, with a minimum of two centimeters of a surrounding underlay about the circumference of the hernia 14. They do so, with sufficient rigidity and with sufficient friction, to eliminate or minimize sliding or migration. When these hernia mesh patches 10 are used by a surgeon, the repair of a patient's inguinal hernia 14, or of another abdominal wall hernia 14, is repaired through a smaller wound or incision 16, with less surgical tension, less post-operative patient discomfort, shorter operation time, and at a potential lower cost to the patient.

I claim:

1. A hernia mesh patch for use in repairing inguinal and other abdominal wall hernias for expansion into a preperitoneal space and direction into a pocket thereof of an abdominal lining, when directed by a surgeon using his or her finger, after being compactively arranged for finger insertion through a relatively small incision, with the patient being usually under minimal anesthesia, and without the need for entering the abdominal cavity, and without the need of complicated instrumentation, such as laparoscopic equipment, comprising:

a. a first layer of inert synthetic mesh material selectively sized and shaped to extend across and beyond a hernia;
   b. a second layer of like material, like size, and like shape of the first layer;
   c. securing means for securing these respective first and second layers nearby their peripheries creating an interior space, serving as a pouch, between these first and second layers;
   d. the pouch, also called a pocket, located between the first and second layers of the inert synthetic mesh material, created when the securing means was used to secure these layers together nearby their peripheries;
   e. wherein one of these layers of inert synthetic mesh material has a transverse slit for the insertion of a single finger into the pouch between these layers, which facilitates the maneuvering and positioning of this hernia mesh patch within a preperitoneal space and its direction into the pocket thereof located by the hernia;
   f. an internally positioned loop, also referred to as a ring or spring, of a non-metallic resilient monofilament fiber, which is compressibly held in the pouch, and thereby creates tension throughout both layers of the inert synthetic mesh material; and
   g. wherein the first and second layers of inert synthetic mesh material, also referred to as the top and bottom layers, each have free outer portions, beyond where the securing means secures them to create the pouch, which are free to frictionally hold the hernia mesh patch in place by under the hernia defect.

2. A hernia mesh patch, as claimed in claim 1, wherein free outer portions are slit to create tab portions thereof to increase their frictional holding power.

3. A hernia mesh patch, as claimed in claim 2, wherein the tab portions are scalloped to increase their frictional holding power.

4. A hernia mesh patch, as claimed in claim 3, wherein the first and second layers of inert synthetic mesh material, inside where the securing means secures the first and second layers together, have spaced aligned openings, which serve to frictionally position the hernia mesh patch and to accommodate the growth of the patient's scar tissue, further insuring the intended positioning of the hernia mesh patch by the hernia.

5. A hernia mesh patch, as claimed in claim 4, wherein the loop, also referred to as the ring or spring, has spaced spikes, which contact the patient's tissue, thereby keeping the hernia mesh patch by the hernia.

6. A hernia mesh patch, as claimed in claim 5, wherein spaced spikes are each located by respective spaced aligned openings in the first and second layers of the inert synthetic mesh material.

7. A hernia mesh patch, as claimed in claim 1, wherein the free outer portions are fringed to increase their frictional holding power.

8. A hernia mesh patch, as claimed in claim 7, wherein the first and second layers of inert synthetic mesh material, inside where the securing means secures the first and second layers together, have spaced aligned openings, which serve to frictionally position the hernia mesh patch and to accommodate the growth of the patient's scar tissue, further insuring the intended positioning of the hernia mesh patch located by the hernia.

9. A hernia mesh patch, as claimed in claim 8, wherein the loop has spaced spikes, which contact the patient's tissue, thereby keeping the hernia mesh patch located by the hernia.

10. A hernia mesh patch, as claimed in claim 9, wherein the spaced spikes are each located by respective spaced aligned openings in the first and second layers of the inert synthetic mesh material.

11. A hernia mesh patch, as claimed in claim 1, wherein the second layer of inert synthetic mesh material has portions thereof made of expanded poly tetra fluoroethylene material, which is used where adhesion to a patient's abdominal viscera is not wanted.

12. A method of sutureless repair of an inguinal or other abdominal wall hernia, and in specific respect to sutureless repair of an inguinal hernia, comprising the steps undertaken by the surgeon of:

a. cutting an approximately three centimeter incision obliquely positioned approximately two to three centimeters above the location described as the internal ring, where the inguinal hernia has occurred, with this cutting extending through the patient's skin, subcutaneous fatty tissues, and the external oblique fascia, which is cut parallel with the fibers thereof a short distance, exposing the underlying internal oblique muscle;
   b. separating portions of the internal oblique muscle to in turn expose the transversalis fascia;
   c. cutting the transversalis fascia creating an entrance into the preperitoneal space above the peritoneum at a location above the hernia;
   d. identifying and freeing the hernia sac;
   e. creating a pocket in the preperitoneal space;

f. obtaining a hernia mesh patch made of a first layer of inert synthetic mesh material selectively sized and shaped to extend across and beyond a hernia, and a second layer of like material, like size, and like shape of the first layer and secured together nearby their peripheries, creating an interior space, serving as a pouch between these first and second layers, and having a transverse slit for the insertion of a single finger of a surgeon into the pouch, and having an internally positioned loop of a resilient monofilament fiber compressibly held in the pouch, which creates tension throughout both layers of the inert synthetic mesh material;

g. folding and compacting the hernia mesh patch;

b. directing the folded and compacted hernia mesh patch down through the incision and beyond into the preperitoneal space;

i. expanding the hernia mesh patch in the preperitoneal space by positioning it so the loop of resilient fiber freely creates the tension throughout both layers of the mesh material;

j. inserting one finger of a surgeon through the incision and beyond to the transverse slit and into the pouch of the hernia mesh patch;

k. directing the hernia mesh patch, by using the finger of the surgeon, through the preperitoneal space and into the pocket by the hernia;

l. withdrawing the surgeon's finger from the hernia patch and back up through the incision; and m. dosing the incision with stitches.

13. A method of sutureless repair of an inguinal or other abdominal wall hernia, as claimed in claim 12, wherein in the step of obtaining a hernia mesh patch includes obtaining a patch having holes made at spaced locations just inside where the layers of the mesh material are secured together, whereby the friction is increased to insure the hernia mesh patch will remain in place, and whereby subsequently the scar tissue will grow through these spaced holes.

14. A method of sutureless repair of an inguinal or other abdominal wall hernia, as claimed in claim 13, wherein the step of obtaining a hernia mesh patch includes obtaining a patch where the layers of inert synthetic mesh material at their peripheries beyond where the layers are secured together are cut to increase their frictional function in keeping the hernia mesh patch in position located by the hernia.

15. A method of sutureless repairing an inguinal and other abdominal wall hernias, as claimed in claim 14, wherein the step of obtaining a hernia mesh patch, includes obtaining a patch, where the internally positioned loop of resilient monofilament fiber is made to include spaced spikes, located at the respective spaced holes, to penetrate the patient's body tissue, to thereby hold the hernia mesh patch in position located by the hernia.

16. A method of sutureless repair of an inguinal or other abdominal wall hernia, as claimed in claim 12, wherein the step of obtaining a hernia mesh patch includes obtaining a patch where the layers of inert synthetic mesh material at their peripheries beyond where the layers are secured together are cut to increase their frictional function in keeping the hernia mesh patch in position located by the hernia.

17. A method of sutureless repair of an inguinal or other abdominal wall hernia, as claimed in claim 12, wherein the step of obtaining a hernia mesh patch, includes obtaining a patch, where the internally positioned loop of resilient monofilament fiber is made to include spaced spikes to penetrate the patient's body tissue, to thereby hold the hernia mesh patch in position located by the hernia.

18. A hernia mesh patch for use in repairing inguinal and other abdominal wall hernias for expansion into a preperitoneal space and direction into a pocket thereof of an abdominal lining when directed by a surgeon using his or her finger, after being compactively arranged for finger insertion through a relatively small incision, with the patient being usually under minimal anesthesia, and without the need for entering the abdominal cavity, and without the need of complicated instrumentation, such as laparoscopic equipment, comprising:

a. a first layer of inert synthetic mesh material selectively sized and shaped to extend across and beyond a hernia;

b. a second layer of like material, like size, and like shape of the first layer;

c. securing means for securing the respective first and second layers nearby their peripheries creating an interior space, serving as a pouch, between these first and second layers;

d. the pouch, also called a pocket, located between the first and second layers of the inert synthetic mesh material created when the securing means was used to secure these layers together nearby their peripheries;

e. a substantially complete transverse slit in one of these layers of inert synthetic mesh for the insertion of a single finger into the pouch between these layers, which facilitates the maneuvering and positioning of this hernia mesh patch within a preperitoneal space and its direction into the pocket thereof located by the hernia; and f. an internally positioned flexible loop, also referred to as a ring or spring, of a non-metallic resilient monofilament fiber, which is compressibly held in the pouch, and thereby creates tension throughout both layers of the inert synthetic mesh material, and this flexible loop is readily handled by a doctor during surgery to change the loop contour for convenient insertion through the incision; yet when the hernia patch is in place, the flexible loop returns quickly to its loop shape.

19. A hernia mesh patch for use in repairing inguinal and other abdominal wall hernias for expansion into a preperitoneal space and direction into a pocket thereof of an abdominal lining when directed by a surgeon using his or her finger, after being compactively arranged for finger insertion through a relatively small incision, with the patient being usually under minimal anesthesia, and without the need for entering the abdominal cavity, and without the need of complicated instrumentation, such as laparoscopic equipment, comprising:

a. a first layer of inert synthetic mesh material selectively sized and shaped to extend across, beyond and under a hernia defect;

b. a second layer of like inert synthetic mesh material, sized, and shaped to extend across and under a hernia defect;

c. a means to secure these respective first and second layers together nearby the periphery of the second layer, creating an interior space, serving as a pouch, between these first and second layers;

d. the pouch, also called a pocket, located between, the first and second layers of the inert synthetic mesh materials, created when these layers are secured together;

e. a substantially complete transverse slit in one of these layers of inert synthetic mesh for the insertion of a single finger into the pouch between these layers, which facilitates the maneuvering and positioning of this hernia mesh patch within a preperitoneal space and its direction into the pocket thereof located by the hernia; and f. an internally positioned flexible loop, also referred to as a ring or spring, of a non-metallic resilient monofilament fiber, which is compressibly held in the pouch, and thereby creates tension throughout both layers of the inert synthetic mesh material, and this flexible loop is readily handled by a doctor during surgery to change the loop contour for convenient insertion through the incision; yet when the hernia patch is in place, the flexible loop returns quickly to its loop shape.

20. A hernia mesh patch, as claimed in claim 19, wherein the second layer of like inert synthetic mesh has spaced openings, nearby where the two layers are secured together, to facilitate tissue growth into this hernia mesh patch.

* * * * *